United States Patent [19]

Leighton et al.

[11] Patent Number: 5,282,404
[45] Date of Patent: Feb. 1, 1994

[54] MICROTOME WITH MICRO-PLANE AND ELECTRIC CONTACT REFERENCE

[75] Inventors: Stephen B. Leighton, Maplewood, N.J.; Alan M. Kuzirian, Cataume, Mass.

[73] Assignee: The Government of the United States of America as represented by the Secretary of the Dept. of Health & Human Services, Washington, D.C.

[21] Appl. No.: 610,880

[22] Filed: Nov. 9, 1990

[51] Int. Cl.$^5$ ............................................. G01N 1/06
[52] U.S. Cl. ........................................ 83/13; 83/42; 83/370; 83/915.5
[58] Field of Search ...................... 83/915.5, 743, 368, 83/370, 821, 823, 42, 703, 707, 13

[56] References Cited

U.S. PATENT DOCUMENTS

| | | | |
|---|---|---|---|
| 664,118 | 12/1900 | Becker . | |
| 1,942,069 | 1/1934 | Setoguchi et al. | 83/575 X |
| 2,292,973 | 2/1941 | Richards | 88/40 |
| 2,680,992 | 8/1950 | Herbain | 88/40 |
| 3,138,749 | 3/1962 | Stibitz | 318/135 |
| 3,225,639 | 2/1964 | Martinelli | 83/915.5 |
| 3,293,972 | 12/1966 | Burkhardt et al. | 83/703 X |
| 3,420,130 | 2/1966 | Farquhar et al. | 83/245 |
| 3,440,913 | 2/1966 | Persidsky et al. | 83/422 |
| 3,496,819 | 10/1967 | Blum | 83/247 |
| 3,799,029 | 3/1974 | Cole et al. | 90/38 R |
| 3,828,671 | 8/1974 | Sitte | 83/703 |
| 3,845,659 | 11/1974 | Wikefeldt et al. | 83/915.5 X |
| 3,975,977 | 8/1976 | Mornberg | 83/707 |
| 4,050,339 | 9/1977 | Soleri | 83/703 |
| 4,163,168 | 7/1979 | Ishikawa et al. | 310/328 |
| 4,377,958 | 3/1983 | Leighton | 83/411 R |
| 4,382,977 | 5/1983 | Murphy et al. | 427/42 |
| 4,436,012 | 3/1984 | Hochanadal | 83/703 |

FOREIGN PATENT DOCUMENTS 57-82743  5/1982  Japan .
63-292036 11/1988 Japan .

OTHER PUBLICATIONS

Cocks et al., "A Cantilever Microtome for Precision Sectioning in Electron and Light Microscopy", *The Review of Scientific Instruments*, vol. 23, No. 11 (Nov., 1952), pp. 615-618.

Echlin et al., "Low Temperature Techniques for Scanning Electron Microscopy", *Conference: Scanning Electron Microscopy*, Part I (Apr. 1976), pp. 753-762.

*Primary Examiner*—Hien H. Phan
*Assistant Examiner*—Ken Peterson
*Attorney, Agent, or Firm*—Lowe, Price, LeBlanc & Becker

[57] ABSTRACT

A microtome for cutting thin sample sections utilizes an electrical contact or sole plate for guiding the section cutting knife during sectioning. The sole plate floats across the surface of the sample thereby ensuring that uniformly thin sections are cut regardless of movement of the sample or expansion or contraction thereof. An electrical contact may be used to detect and reference contact between the sample surface and the section cutting knife. After contact between the sample surface and section cutting knife is referenced, the relative position between the sample surface and section cutting knife may be adjusted to achieve a desired section thinness.

17 Claims, 3 Drawing Sheets

MICROTOME WITH MICRO-PLANE AND ELECTRIC CONTACT REFERENCE

TECHNICAL FIELD

The present invention relates to microtomes, and more particularly to a microtome having a micro-plane or an electric contact reference.

BACKGROUND ART

For many applications in the fields of biology, medicine, and pharmacology, very thin sections of tissue from living animals are necessary, e.g., for microscopic examinations. To cut such sections, specialized precision cutting apparatuses called microtomes are employed.

Specimens from which tissue sections are to be cut are prepared by various techniques, e.g., by embedding the specimen in paraffin wax, plastic, or other suitable solid matrix which has the proper degree of hardness for sectioning with a glass knife. A further known method for specimen preparation is the so-called cryostat method in which the specimen is frozen and sectioned in the frozen state.

In preparing biological specimens for electron microscopes, it is essential that very thin sections of tissue be cut in order to properly examine the specimen. It is often desirable that ultra-thin sections of a thickness on the order of 200 to 300 Angstrom units or less be cut from biological tissue. Ultra-thin sections must be cut without distorting the specimen through compression of the tissue or scoring of the tissue by the cutting tool edge.

In preparing specimens for an electron microscope, a microtome having a knife formed from plate or window glass (or diamond) is utilized to section the specimen into very thin pieces. To form the knife, the plate or window glass is fractured to expose a sharp edge.

After the biological specimen has been prepared for sectioning, the embedded specimen is secured to the specimen holder of a microtome. The microtome causes the knife edge to contact the specimen so that very thin sections of the specimen are sliced therefrom.

Advances in microtomes involve the mechanical structure which produces the relative movement between the specimen and knife to section the specimen, and the manner in which the specimen is supported.

U.S. Pat. No. 664,118 discloses a microtome wherein a horizontally movable slicing knife (B) is clamped to a supporting bar (C). The bar is pivotally connected to horizontally-swinging arm (D and D'). Movement is actuated by a horizontally-swinging hand lever (F). The specimen is frozen on the supporting block (G) and the support can be raised or lowered toward the knife by a screw.

U.S. Pat. No. 2,292,973 discloses a microtome mounted on supports such that when handle (19) is moved back and forth, swinging arms (14 and 15) for the knife and swinging arms (12 and 13) from the support, join together to form a parallelogram so that the object to be sliced always remains in the same position. The sections are also uniform in thickness as the set screw is automatically turned for raising the supporting block after each cut by the hatch and pawl mechanism on the support (6).

U.S. Pat. No. 2,680,992 discloses an apparatus for slicing organic tissue wherein a blade (4) is placed in a reciprocating frame (5) so that a slice of tissue is made with each downward stroke. The tissue is placed in a cylindrical chamber (26) and pressed against a specimen support (3) after first being placed in a chamber and cooled. A slot (27) is formed between the chamber and specimen holder (3) through which the knife passes.

U.S. Pat. No. 3,420,130 shows a microtome with synchronized cutting and feeding operations. The motor revolves a screw shaft (53 and 71) which revolves to advance a carriage (21) carrying the specimen. Simultaneously, the cam shaft (39) rotates and with it the cam follower (86) carrying the knife lever (82). The knife lever carries the blade (103) and cyclically oscillates in an arc. The cam follower is held in close relationship by spring (87) engaging a pin (88), projecting from the knife lever, and by one adjusting screw (89). Whenever a cut is made on the block the carriage containing the specimen is stationary.

U.S. Pat. No. 3,440,913 teaches using a reciprocating knife for making cuts on a specimen wherein the knife edge moves transversely with respect to the specimen. Within casings (2 and 2') are a pair of leaf springs (4 and 4') attached by screws (5) to the inner wall of the casings. A shaft (3) is fixed on the springs and carries the blade holder (17). The shaft oscillates along its longitudinal axis by virtue of the transverse flexure of springs. The speed, frequency and amplitude of operation can be varied. The specimen is moved into the vibrating blade and after this operation the specimen carriage is returned and the knife stopped so that the section will float clear of the specimen.

U.S. Pat. No. 3,496,819 is another example of an oscillating knife for sectioning tissues mounted on an intermittently moving stage. The apparatus is similar to that of U.S. Pat. No. 3,420,130 above. The thickness of sections cut by knife (136) is controlled by a knob (216) (FIG. 2) which sets into play a series of motions which determines the transverse distance of the disc (226) upon which the specimen is resting.

U.S. Pat. No. 3,799,029 teaches reciprocating a knife along a slanted table for trimming a specimen prior to microtoming. A carriage assembly is mounted to a base and the reciprocating knife is attached to the assembly (19) to reciprocate therewith. The specimen is mounted in a vertical shaft (43) which can be turned to make different cuts by a goniometer. The carriage assembly is supported from two guide rails (53a and 53b) on two parallel arrays of bearings (57).

U.S. Pat. No. 3,975,977 teaches a crank (13) for downward movement of knife (7) and frame (79) and guides (11 and 12). The knife is set for automatic downward movement at a predetermined distance corresponding to the desired thickness to be taken from the object (3) upon movement of carriage (1) to the right.

Russian Patent No. 638,862 discloses the use of piezoelectric effects for fine adjustment of a specimen holder.

The publication "A Cantilever Microtome for Precision Sectioning in Electron and Light Microscopy", *The Review of Scientific Instruments*, Vol. 23, No. 11 (November 1952), pages 615–618, discloses a cantilever microtome wherein either the specimen or the knife may be mounted on the cantilever while the other is rigidly attached to the frame supporting the cantilever.

Despite advances in the art of microtomes, an existing problem associated with microtomes is that specimen blocks may often expand or contract unpredictably between cuts, especially in the case of thermal expansion due to thermal inputs to the specimen block. As a result of unpredictable expansion or contraction of the specimen, section thickness will not be accurate, and can in fact be unsuitable for desired examination procedures.

Accordingly, there exists a need for microtomes which produce accurate sectioning thickness regardless of unpredictable expansion or contraction of the specimen.

DISCLOSURE OF THE INVENTION

It is accordingly one object of the present invention to provide a microtome which compensates for unpredictable expansion or contraction of specimens to be sectioned.

It is another object of the present invention to provide a microtome which sets and adjusts section cutting thickness by referencing the surface of the specimen.

Another object of the present invention is to provide a microtome having an electrical contact means which references the position of the surface of the specimen.

A further object of the present invention is to provide a microtome having a knife that is guided during section cutting by the surface of the specimen.

A still further object of the present invention is to provide a microtome which is sufficiently compact so as to positionable within a scanning electron microscope (SEM).

A still further object of the present invention is to provide a microtome which automatically adjusts the thickness of sectional cutting to compensate for any expansion or contraction of specimens to be sectioned.

An even further object of the present invention is to provide a method of sectioning a specimen which compensates for unpredictable expansion or contraction of specimens to be sectioned.

According to these and other objects of the present invention the present invention provides an apparatus for cutting thin sections from a sample to be sectioned which includes means to support a sample to be sectioned and means to reference the position of a surface of a sample located on the sample support means with respect to a section cutting knife, which surface position referencing means includes means to contact the surface of the sample located on the sample support means.

The present invention also provides a microtome including a sample supported in a sample support, a section cutting knife, and an electrical contact detection means for referencing the position of the surface of the sample with respect to the section cutting knife. The electrical contact detection means includes conductive contacting surfaces on the sample and the section cutting knife and an electrical circuit for detecting contact between the sample and the section cutting knife.

The present invention further provides a method of cutting thin sections from a biological sample which involves initially contacting the surface of a biological sample to establish a reference position with respect to the surface of the sample and thereafter sectioning the sample at a predetermined thickness.

BRIEF DESCRIPTION OF DRAWINGS

Aspects of the present invention will be described with reference to the annexed drawings, which are given by way of non-limiting examples, in which.

BEST MODE FOR CARRYING OUT THE INVENTION

Figure 1:
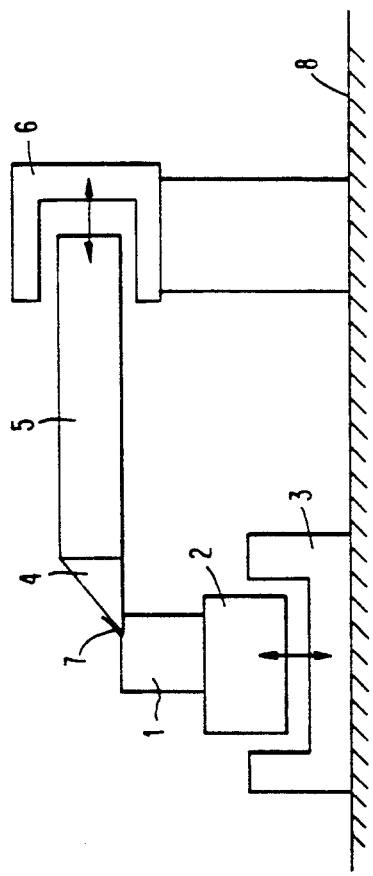
FIG. 1 is a schematic vertical cross-sectional block diagram of a prior art microtome illustrating the kinetics involved with sectioning a specimen block.

The present invention relates to a microtome which includes means to contact and thereby reference the surface of a specimen block to be sectioned. According to one embodiment of the present invention the contacting means includes a sole plate which, after contacting the specimen block, remains in contact with the specimen block during each cutting stroke during which a section cutting knife coupled to the sole plate moves relative to the specimen block to affect sectioning of the specimen block.

According to another embodiment of the present invention the contacting means includes an electrically conductive section cutting knife which is connected to an electrical contact detection means which detects contact between the section cutting knife and the specimen block. In each cycle, the relative position of the surface of the specimen block is initially detected by means of the electrical contact detection means. Thereafter, the position of the section cutting knife with respect to the specimen block surface is properly adjusted an appropriate distance to produce a desired section thickness when the section cutting knife or specimen block is moved through a cutting stroke.

In one embodiment, the present invention relates to a microtome which utilizes the principle of a carpenter's plane to control the section thickness during cutting. Specifically, a sole plate is provided which slides along the surface of a specimen block face.

The sole plate supports a section cutting knife in a position wherein the cutting edge of the knife protrudes a controlled distance beyond the lower surface or plane of the sole plate. The distance at which the cutting edge of the knife protrudes beyond the lower surface or plane of the sole plate is proportional to the thickness at which the specimen section is cut.

In the present invention, the specimen block is held in a fixed position by a specimen block support means of the known type. Because the thickness of the section cutting is controlled by adjusting the position of the section cutting knife relative to the sole plate, movement of the specimen block is irrelevant and unnecessary. During a sectioning or cutting stroke the sole plate supporting the section cutting knife "floats" block face. Therefore, section cutting is performed at a constant thickness regardless of the motion of the specimen block.

The position of the section cutting knife is preferably adjusted by both a course and fine adjustment. Although each adjustment may be performed by automated means, the course adjustment is preferably a manual screw thread or similar adjustment means.

The fine adjustment means utilized in the microtome of the present invention includes a piezoelectric crystal which enables fine continuous positional control of the section cutting knife with respect to the sole plate with no thermal effects.

Relative movement between the section cutting knife/sole plate assembly and the supported specimen required to section or cut the specimen is provided by a suitable driving means such as an electric motor which pushes the section cutting knife/sole plate assembly through a cutting stroke by means of a suitable mechanical linkage, e.g., an eccentric crank arm linkage. Alternately, a fluid operated piston or bellows may be utilized to drive the section cutting knife/sole plate assembly through the cutting stroke.

In order to insure that the sole plate is loaded, i.e., is in contact with the surface of the specimen block during the section cutting, the section cutting knife/sole plate assembly is spring biased against the specimen block. As will be discussed in detail below, cooperating movement between the elements of the microtome of the present invention is controlled by a number of flexible hinges.

The manner in which the section cutting knife is moved with respect to the specimen and the manner in which the thickness of the sectioning is adjusted provides a microtome which is more compact than conventional microtomes. Being more compact and adapted for automated or semiautomated operation, the microtome of the present invention may be easily incorporated and utilized in automated or semiautomated measuring instruments such as optical microscopes, scanning electron microscopes, or similar instruments.

According to another embodiment of the present invention an electrical contact means is provided which references the position of the surface of the specimen block. The electrical contact means includes a conductivity detecting circuit which is provided to detect and determine when the section cutting knife initially contacts the specimen block. Accordingly, the contacting surfaces of both the section cutting knife and the specimen are made conductive and connected to a simple conductivity detecting circuit which includes means such as a conductivity meter for detecting conductivity.

By utilizing the electrical contact means to initially reference the position of the surface of the specimen block with the section cutting knife, it is possible to more accurately control the thickness of the section. Thus, in operation the position of the surface of the specimen block is initially determined. Thereafter, the position of the section cutting knife, may be adjusted to achieve the desired section thickness. In this manner, the position of the section cutting knife may be adjusted at the beginning of a series of sectioning cuts of before each individual sectioning cut.

Reference will now be made to the drawings wherein, wherever possible, corresponding reference numerals indicate similar elements.

FIG. 1 is a schematic vertical cross-sectional block diagram of a prior art microtome illustrating the kinetics involved with sectioning a specimen block. In FIG. 1, reference numeral 1 indicates a specimen block which includes a tissue sample embedded in a solid matrix of the known type. The specimen block is held by a support 2, which in most conventional microtomes is movable by an advancing means 3 which adjusts the thickness of a section cut by moving the specimen block along the directions indicated by the double headed direction arrow.

The section cutting knife 4 is held by a knife support 5 which, in most conventional microtomes is movable by a driving means 6, which reciprocally moves knife 4 through a section cutting stroke in which a thin section 7 is cut from specimen block 1. The double headed direction arrow connecting knife support 5 and driving means 6 indicates the directional movement of the knife support 5 and knife 4. The above-described elements of the microtome are attached to a common base 8.

Figure 2:
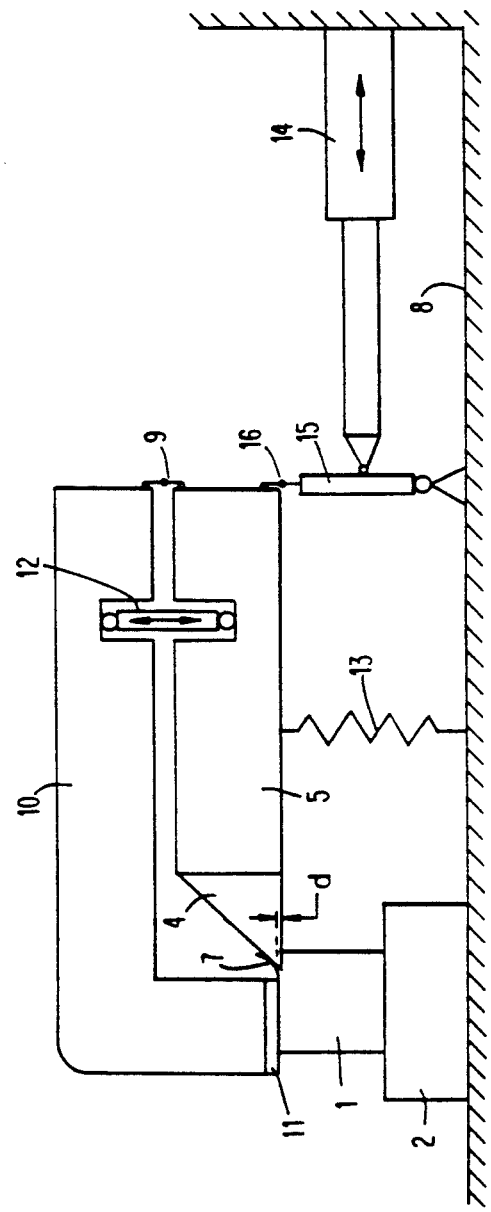
FIG. 2 is a schematic vertical cross-sectional block diagram of a microtome according to one embodiment of the present invention illustrating the kinetics involved with sectioning a specimen block.

FIG. 2 is a schematic vertical cross-sectional block diagram of a microtome according to one embodiment of the present invention illustrating the kinetics involved with sectioning a specimen block. In FIG. 2 the specimen block 1 which includes a frozen tissue sample or a tissue sample embedded in a solid matrix of the known type, e.g., plastic, is held by a support 2. In the present invention, support 2, which may be of conventional design is held in a fixed position of base 8.

Section cutting knife 4 is replaceably attached to knife support 5 which is connected via flexible hinge 9 to sole plate support 10. A sole plate 11 which is designed to "float" along the surface of specimen block 1 is attached to the sole plate support 10.

The section cutting knife/sole plate assembly, in addition to including the section cutting knife 4, knife support 5, flexible hinge 9, sole plate support 10 and sole plate 11, also includes a section thickness adjustment means 12 which, as described in detail below with reference to FIG. 3, includes both a course and fine adjustment means for adjusting the distance "d" at which blade edge of section cutting knife 4 projects below the lower plane of the sole plate 11. Flexible hinge 9 maintains the proper alignment of the section cutting knife/sole plate assembly while allowing for necessary changes in distance "d" between the blade edge of the section cutting knife 4 and the lower plane of the sole plate 11.

In order to ensure that the sole plate 11 is loaded, i.e., is in contact with the surface of the specimen block during the section cutting the section cutting knife/sole plate assembly is spring biased against the specimen block by suitable spring means 13. Spring means 13 is illustrated as being located between knife support 5 and base 8. However, the spring means 13 could be located and connected to any portion of the section cutting knife/sole plate assembly and the base 8 or support 2.

The section cutting knife/sole plate assembly is driven through a cutting stroke by a suitable driving means 14, which may comprise a controlled reciprocating fluid operated piston or bellows. In a preferred embodiment discussed below in reference to FIG. 3 below, the driving means comprises an electric motor which pushes the section cutting knife/sole plate assembly through a cutting stroke by means of an eccentric crank arm linkage.

Motion from the driving means 14 is transferred to support arm 15 which as illustrated in FIG. 2 is connected between base 8 and the section cutting knife/sole plate assembly. In a preferred embodiment, a flexible hinge is utilized to connect support arm 15 to the section cutting knife/sole plate assembly.

Figure 3:
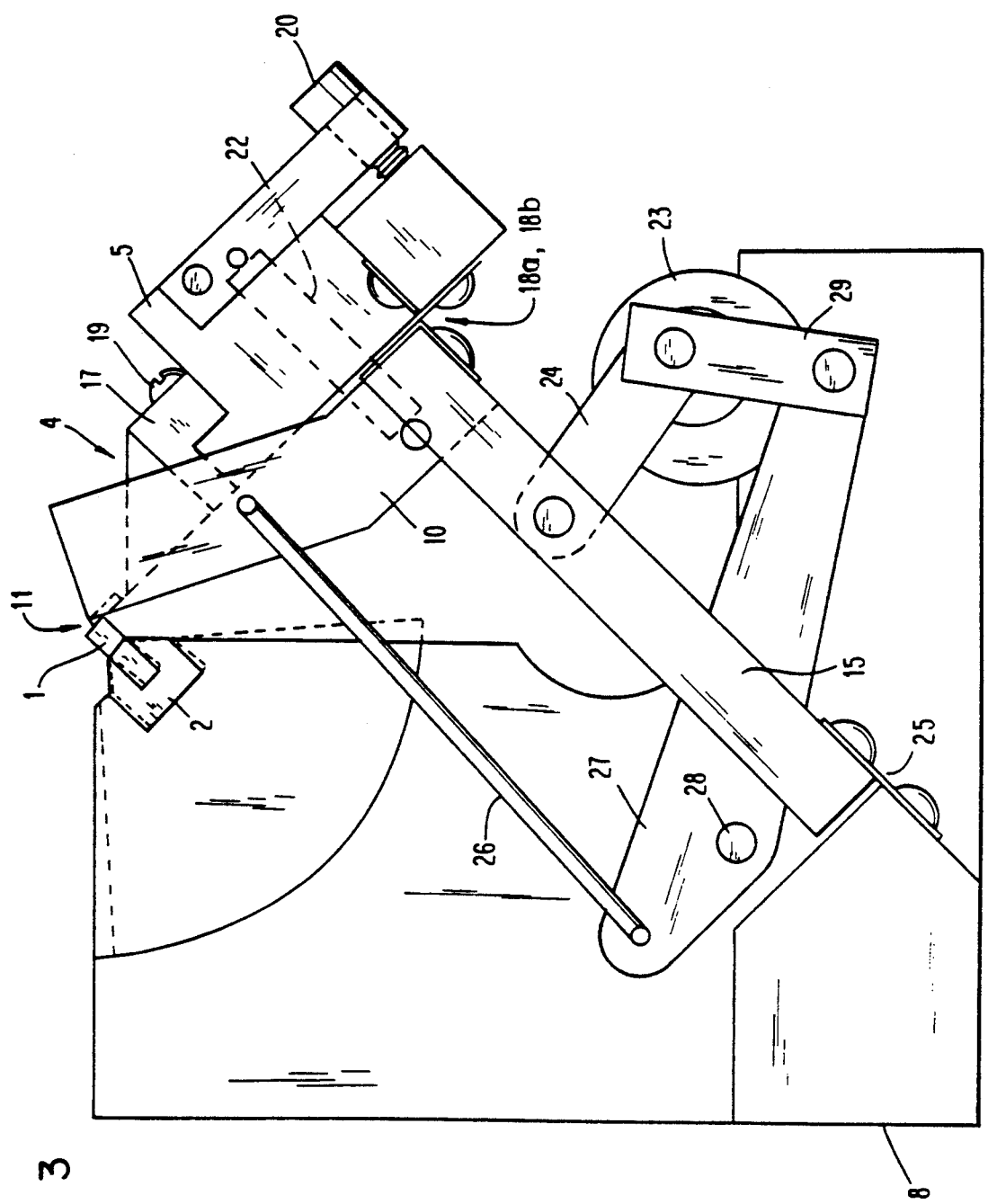
FIG. 3 is a schematic vertical cross-sectional view of a microtome according to one embodiment of the present invention.

FIG. 3 is a schematic vertical cross-sectional view of a microtome according to one embodiment of the present invention. In FIG. 3 the specimen block 1 which includes a tissue sample embedded in a solid matrix of the known type, is held by a support 2. In a preferred embodiment of the present invention illustrated in FIG. 3, the specimen support 2 is tiltable with respect to the base 8 (as indicated by phantom lines in the figure) so that various section angles of the specimen may be presented to the section cutting knife/sole plate assembly.

Section cutting knife 4, which comprises a conventional glass microtome knife is replaceably attached by attachment means 17 to knife support 5 which is connected via flexible hinges 18a and 18b to sole plate support 10. As illustrated in FIG. 3 attachment means 17 may be a clamp which secures section cutting knife 4 to knife support 5 by means of a threaded screw or similar means 19. A sole plate 11 which is designed to "float" along the surface of specimen block 1 is attached to the sole plate support 10. As illustrated in FIG. 3, the sole plate support includes an upper cut out portion in which section cutting knife 4 is positioned adjacent sole plate 11.

The section cutting knife/sole plate assembly of FIG. 3 includes both a course and fine section thickness adjustment means. The course section thickness adjustment means comprises a threaded member 20 which freely rotates in an upper portion of the knife support and which coacts with internal threads of member 21 which is connected by flexible hinge 18a and 18b to sole plate support 10. By manually rotating threaded member 20, the relative distance between the blade edge of section cutting knife and the lower plane of the sole plate can be coarsely adjusted.

For fine section thickness adjustment a piezoelectric crystal assembly 22 is provided between knife support 5 and sole plate support 10, as illustrated. Fine adjustments of the section thickness are provided by applying suitable d.c. voltages across top and bottom electrodes (not illustrated) of the piezoelectric crystal assembly 22.

Relative movement between the section cutting knife/sole plate assembly and the supported specimen block 1 required to section the specimen block 1 is provided by a suitable driving such as an electric motor 23 which pushes the section cutting knife/sole plate assembly through a cutting stroke by means of an eccentric crank arm linkage assembly as illustrated. The eccentric arm linkage assembly includes arm 24 which connects and transfers reciprocating motion to support arm 15 which is connected by flexible hinges 25, 18a and 19b to base 8, and the section cutting knife/sole plate assembly as illustrated.

In order to insure that the sole plate is loaded, i.e., is in contact with the surface of the specimen block during the section cutting, the section cutting knife/sole plate assembly is spring biased against the specimen block by means of spring loaded biasing arm 26. In order to ensure that the sole plate is lifted over and passed the surface of the specimen block during return motion of the section cutting stroke, spring loaded biasing arm 26 is connected between a pivotal linkage arm 27 and sole plate support 10. In operation, pivotal linkage arm 27 pivots about pivot element 28, e.g., a pin located on base 8, as motion thereto is applied by eccentric linkage member 29.

Although not illustrated, the movement of the microtome as described above with reference to FIGS. 2 and 3 may be effected and controlled by conventionally known means, including computer control means.

Figure 4:
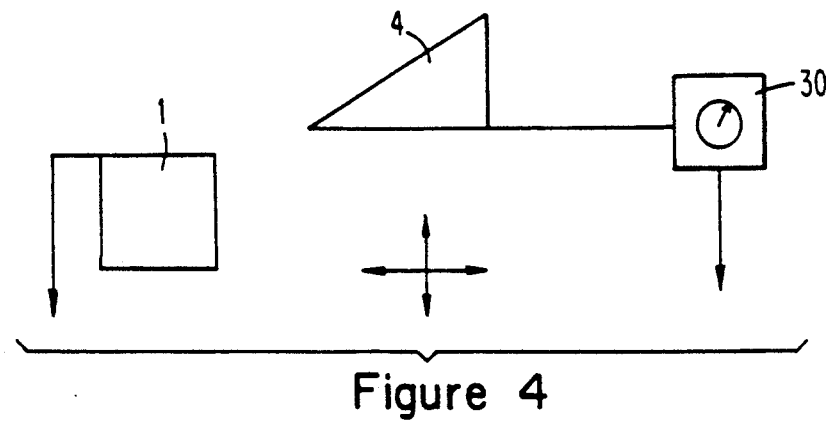
FIG. 4 is a schematic block diagram of a microtome according to one embodiment of the present invention illustrating the kinetics involved with sectioning a specimen block.

FIG. 4 is a schematic block diagram of a microtome according to an embodiment of the present invention illustrating the kinetics involved with sectioning a specimen block utilizing a microtome having an electrical contact means which references the position of the surface of the specimen. In the embodiment of the microtome illustrated in FIG. 4, the underside of the microtome knife 4 is provided with an electrically conductive coating, such as chromium or tungsten. Likewise, the surface of the specimen block 1 is made conductive either by en-bloc stain or by a sputtering process utilized to image the specimen in a scanning electron microscope system.

The specimen is grounded, and the electrically conductive portion of the knife 4 is isolated from the ground and connected to a continuity tester 30, e.g., conductivity meter, or an automated controller which effects operation of the microtome in the manner discussed below. In this arrangement, the continuity tester 30 operates to indicate the instance when the underside of the knife 4 contacts the surface of the specimen block 1.

Utilizing the embodiment of the present invention illustrated in FIG. 4, the section cutting knife 4 is moved in relationship to specimen block 1 in a controlled sequence of directions (generally indicated by the illustrated directional cross arrows) in an automated or semiautomated manner as described below.

FIGS. 5a-5f are schematic block diagrams illustration the operation of a microtome utilizing the electrical contact referencing means of FIG. 4. Although not illustrated, the movement of the microtome as described below may be effected and controlled by conventionally known control means, including computer control.

Figure 5A:
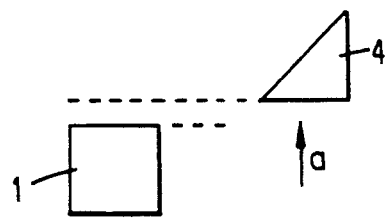
FIGS. 5a–5f are schematic block diagrams illustrating the operation of a microtome utilizing the electrical contact referencing means of FIG. 4.

In FIG. 5a the section cutting knife 4 and specimen block 1 are illustrated in relative positions with the section cutting knife 4 in a retracted position of the section cutting stroke. In this position, the section cutting knife 4 is moved in the direction indicated by directional arrow "a" to a position where the cutting plane of the section cutting knife 4 is above a surface of specimen block 1.

Figure 5B:
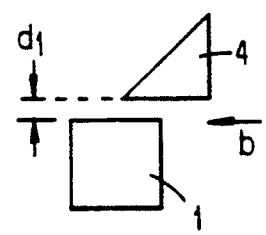

In FIG. 5b the section cutting knife 4 is illustrated as being moved in a direction indicated by directional arrow "b" to a position over the upper surface of the specimen block 1.

Figure 5C:
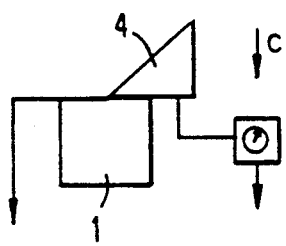

In FIG. 5c, with the section cutting knife 4 positioned over the upper surface of specimen block 1, the section cutting knife 4 is lowered or moved toward the specimen block 1 in one direction illustrated by directional arrow "c" a distance "$d_1$" (illustrated in FIG. 5b) until the conductivity tester 30 detects contact between the lower surface of the section cutting knife 4 and the specimen block 1.

Figure 5D:
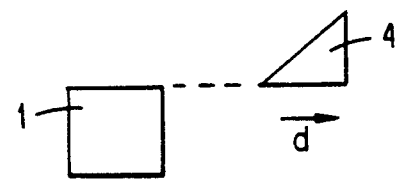

In FIG. 5d the section cutting knife 4 is moved to a retracted position from the specimen block 1 in a direction indicated by directional arrow "d" without further movement from or to the specimen block 1 in the direction indicated by directional arrows "a" or "c".

Figure 5E:
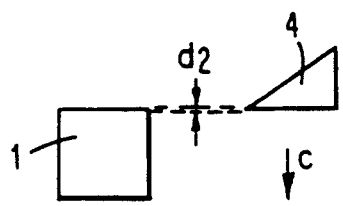

In FIG. 5e the section cutting knife 4 is maintained in a retracted position and moved in a direction indicated by directional arrow "c" a distance "$d_2$" which corresponds to the section cutting thickness.

Figure 5F:
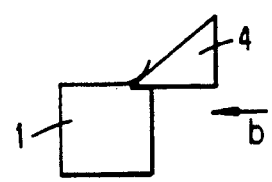

In FIG. 5f the section cutting knife 4 is moved in a direction indicated by directional arrow "b", without further movement from or to the specimen block 1 in the direction indicated by directional arrows "a" or "c", through a section cutting stroke in which a thin section 7 is cut from the specimen block 1.

After cutting the section as illustrated in FIG. 5f, the steps illustrated in FIG. 5a-5f may be repeated as necessary.

The embodiment of the microtome illustrated and discussed in reference to FIGS. 4 and 5a-5f may be utilized in most conventional microtomes. In this regard, when incorporating this embodiment into a microtome which adjusts the section cutting thickness by moving the specimen block 1, the specimen block 1 must be moved as necessary along the directions indicated by directional arrows "a" and "c".

Although the contact of the section cutting knife with the specimen block is described, for illustrative purposes as utilizing detection of conductivity, it is within the scope of the present invention to utilize other electrical properties, particularly capacitance and tunnelling current, e.g. as in the case of scanning tunnelling microscopes.

The microtomes of the present invention have been found to provide a significant advantage over existing microtomes. In particular, utilizing the microtomes of the present invention, thinner and more uniform cut sections can be made regardless of any movement of the specimen block or any expansion or contraction of the specimen block. The microtomes of the present invention can be easily automated and can be made more compact than existing microtomes, thus allowing direct incorporation and use in measuring instruments such as optical microscopes and electron scanning microscopes.

The invention has been described herein with reference to certain preferred embodiments. However, as obvious variations thereon will become apparent to those skilled in the art, the invention is not to be considered as limited thereto.

What is claimed is:

1. In a microtome including a sample supported in a sample support and a section cutting knife, the improvement comprising an electrical contact detection means for referencing a position of a surface of the sample with respect to said section cutting knife, including conductive contacting surfaces on the sample and said section cutting knife and an electrical circuit for detecting contact between the sample and said section cutting knife.

2. A microtome according to claim 1, further including means to provide relative movement between the sample and said section cutting knife in at least two orthogonal directions.

3. A microtome for cutting thin sections from a sample to be sectioned which comprises means to support a sample to be sectioned and means to contact and thereby reference a position of a surface of a sample located on said sample support means with respect to a section cutting knife, which surface position referencing means comprises means to contact the surface of the sample located on said sample support means, wherein said sample surface contacting means comprises a section cutting knife/sole plate assembly including a sole plate, said section cutting knife and means to support said section cutting knife.

4. A microtome for cutting thin sections from a sample to be sectioned according to claim 3, wherein said sample contacting means comprises an electrical conductive portion of said section cutting knife.

5. A microtome for cutting thin sections from a sample to be sectioned according to claim 3 wherein said sample support means is held in a fixed position to a base and means for moving said section cutting knife relative to said sample support means is provided.

6. A microtome for cutting thin sections from a sample according to claim 5 wherein said sample support means is tiltably attached to said base.

7. A microtome for cutting thin sections from a sample according to claim 3 wherein said section cutting knife/sole plate assembly further includes a sole plate support which is adjustably movable with respect to said section cutting knife support to thereby adjust the distance at which said section cutting knife extends beyond said sole plate 8. A microtome for cutting thin sections from a sample according to claim 7, wherein said sole plate support and said section cutting knife support are movable adjustable with respect to each other by means of a course and a fine adjustment means each of which is located between said sole plate and section cutting knife supports.

9. A microtome for cutting thin sections from a sample according to claim 8, wherein said course adjustment means comprises means for manually adjusting the relative position between said sole plate support and said section cutting knife.

10. A microtome for cutting thin sections from a sample according to claim 9, wherein said fine adjustment means comprises a piezoelectric crystal.

11. A microtome for cutting thin sections from a sample according to claim 3, further including a base to which said sample support means is attached and a spring biasing means connected between said base and said section cutting knife/sole plate assembly for loading said sole plate on the surface of the sample.

12. A microtome for cutting thin sections from a sample according to claim 11, further including means to move said sole plate away from the sample when said section cutting knife/sole plate assembly is moved in a direction opposed to the cutting stroke.

13. A microtome for cutting thin sections from a sample according to claim 12, wherein said means for moving said sole plate from the sample comprises a spring loaded biasing arm connected between said section cutting knife/sole plate assembly and a pivotal linkage arm, said pivotal linkage arm being further connected by an eccentric linkage member to said drive means.

14. A microtome for cutting thin sections from a sample according to claim 3, further including means to drive said section cutting knife through a section cutting stroke wherein said means to drive comprises an electric motor and eccentric linkage means connected to said section cutting knife/sole plate assembly by means of a support arm.

15. A method of cutting thin sections from a biological sample which comprises contacting a surface of a biological sample with a knife of a microtome to establish a reference position with respect to said surface of said sample and thereafter sectioning said sample at a predetermined thickness utilizing said microtome.

16. A method of cutting thin sections from a biological sample according to claim 15, comprising detecting initial electrical contact between said sample and said knife by means of an electrical circuit and, after said detection, adjusting the relative position between said knife and said sample prior to cutting.

17. A method of cutting thin sections from a biological sample according to claim 15, wherein said sample is frozen.

* * * * *